(12) United States Patent
Fleming et al.

(10) Patent No.: US 10,242,391 B2
(45) Date of Patent: Mar. 26, 2019

(54) SYSTEM FOR CREATING CUSTOM FRAGRANCES

(71) Applicants: Danielle K. Fleming, Dunmore, PA (US); Michael W. Sherwin, Moscow, PA (US)

(72) Inventors: Danielle K. Fleming, Dunmore, PA (US); Michael W. Sherwin, Moscow, PA (US)

(*) Notice: Subject to any disclaimer, the term of this patent is extended or adjusted under 35 U.S.C. 154(b) by 516 days.

(21) Appl. No.: 14/936,662

(22) Filed: Nov. 9, 2015

(65) Prior Publication Data
US 2016/0132950 A1  May 12, 2016

Related U.S. Application Data

(60) Provisional application No. 62/078,944, filed on Nov. 12, 2014.

(51) Int. Cl.
*G06Q 30/00* (2012.01)
*G06Q 30/02* (2012.01)
(Continued)

(52) U.S. Cl.
CPC ........ *G06Q 30/0281* (2013.01); *A61Q 13/00* (2013.01); *C11B 9/00* (2013.01);
(Continued)

(58) Field of Classification Search
None
See application file for complete search history.

(56) References Cited

U.S. PATENT DOCUMENTS 3,696,161 A * 10/1972 Kobetz ............... C07C 2/88
556/186

5,031,764 A * 7/1991 Meador ............... A45D 34/02
206/232
(Continued)

OTHER PUBLICATIONS

Wood, Dana, Perfumer's Workshop to Launch Custom Scents, Fairchild Publications, Sep. 7, 1990 (Year: 1990).*

*Primary Examiner* — William J Allen
*Assistant Examiner* — Timothy J Kang
(74) *Attorney, Agent, or Firm* — Lawrence P. Zale; Zale Patent Law, Inc.

(57) ABSTRACT

A system for creating custom fragrances is described that allows a customer to interact with an employee and a Perfumer's Organ to interactively select several scents for base, middle and top notes. They can then iteratively adjust the scents chosen. In one embodiment, the scents selected by a customer are provided to a computing device having a prestored table which separates the scents into variable potency scents having variable perceived strengths and normal potency scents having standard, equal perceived strengths. The table indicates the amount of each variable potency scent to use to normalize the strengths. The remaining normal potency scents are then added with an equal amount. In an alternative embodiment, predetermined mixtures are provided to the computing device and used as 'training data' to adjust the coefficients of a generalized formula to create a prediction equation fit to the training data. The computing device receives the selected scents, the type of product to be made and the container size and uses the prediction equation to identify the amounts of each of the selected scents. In another optional embodiment, a filling device can automatically meter the scent liquids, a filling material, and provide them into the selected container. The filling device is driven by the computing device and determines the amounts of the selected scents and creates the custom fragrance according to one of the methods above.

12 Claims, 9 Drawing Sheets

(51) Int. Cl.
*G06Q 30/06* (2012.01)
*C11B 9/00* (2006.01)
*G06Q 10/08* (2012.01)
*A61Q 13/00* (2006.01)

(52) U.S. Cl.
CPC ......... *G06Q 10/0832* (2013.01); *G06Q 30/06* (2013.01); *G06Q 30/0621* (2013.01)

(56) References Cited

U.S. PATENT DOCUMENTS

| | | | |
|---|---|---|---|
| 5,626,155 | A | 5/1997 | Saute |
| 6,402,120 | B1 | 6/2002 | Swaab |
| 6,516,245 | B1 | 2/2003 | Dirksing et al. |
| 6,800,015 | B1* | 10/2004 | Derges .................... A61L 9/042 239/211 |
| 2003/0014324 | A1 | 1/2003 | Donovan et al. |
| 2003/0166499 | A1* | 9/2003 | Yang ........................ A61K 8/31 512/1 |
| 2008/0027820 | A1 | 1/2008 | Brill |
| 2008/0131858 | A1* | 6/2008 | Gordon .............. G09B 19/0076 434/327 |
| 2009/0068068 | A1* | 3/2009 | Harris ...................... A61L 9/03 422/125 |
| 2009/0156501 | A1* | 6/2009 | Brann .................. G01N 33/942 514/1.1 |
| 2010/0049636 | A1* | 2/2010 | Sawada ................ G06Q 10/087 705/28 |
| 2014/0032356 | A1 | 1/2014 | Chuang et al. |
| 2015/0182578 | A1* | 7/2015 | Cavallaro ............ A61K 36/886 424/734 |

\* cited by examiner

SYSTEM FOR CREATING CUSTOM FRAGRANCES

CROSS REFERENCE TO RELATED APPLICATIONS

This application claims the benefit of U.S. Provisional Patent Application "SYSTEM FOR CREATING CUSTOM FRAGRANCES" Ser. No. 62/078,944 filed Nov. 12, 2014, by Danielle K. Fleming and Michael W. Sherwin, and hereby incorporates it by references in its entirety.

BACKGROUND OF THE INVENTION

1. Field of the Invention

The current invention relates to a system for creating custom fragrances, and specifically to a system for creating custom fragrances in an objective and repeatable process.

2. Discussion of Related Prior Art

The vast majority of fragrances are made by specific formulas that are mass marketed to the public. These fragrances may be made into perfumes and colognes, lotions, soaps, body washes and other personal hygiene products. These are usually determined by the companies and not custom made by the customer.

There have been some attempts to allow a user to make custom products such as U.S. Pat. No. 6,402,120 B1 Swaab, Jun. 11, 2002, "Apparatus for Blending and Fabricating Personalized Lipstick". This deals with custom color for lipstick and does not deal with the creation of custom fragrances.

U.S. Patent Application 2008/0027820 A1 Brill, Jan. 31, 2008, "Methods and Systems for the Creation of Consumer-Customization and Commercialization of Goods" discloses customization of wines but does not disclose any description of how to customize fragrances.

U.S. Patent Application 2014/0032356 A1 Chuang et al., Jan. 30, 2014, "Method and System for Selling Custom Products" deals with the general idea of customization of products, but requires the customer to send their customization preferences to a central server. Obviously, there is no way to electronically sample fragrances, so this cannot apply to the customization of fragrances.

U.S. Pat. No. 6,516,245 B1 Dirksing et al., Feb. 4, 2003, "Method for Providing Personalized Cosmetics" and U.S. Patent Application 2003/0014324 A1 Donovan et al., Jan. 16, 2003, "Techniques for Synthesizing and Distributing Personal Care Products" have a similar problem as Chuang above, being that there is no way of remotely sampling scents.

U.S. Pat. No. 5,031,764 Meador et al., Jul. 16, 1991, "Apparatus for Designing Personalized Perfume" discloses a group of blotters held together as a single unit for sampling scents. However, blotters are not intended to be added or deleted and therefore can only be used as a fixed group of scents.

US Patent Application 2008/0131858 A1 Gordon, Jun. 5, 2008, "Method and Apparatus for Creating a Custom Blended Fragrance" describes a method of creating custom fragrances based upon a personality test. This tends to be very subjective and not accurate.

U.S. Pat. No. 5,626,155 Saute, May 6, 1997, "Method of Creating Fragrances In Situ" requires that the mixed scents be applied on the customer's skin. This will only apply to fragrances mixed in-situ.

These attempts to create perfumes are typically subjective and random. A user would simply smell various scents and mix them without regard to groupings or volatility of the scent. In which case, some fragrances would dominate the others or the end result of the fragrance composition would be poorly structured thus not having an appealing odor.

There was also little consideration given to the time-changing aspects of the fragrance. Therefore, a fragrance which is initially appealing may become less appealing over the course of the day.

Also, there has been little effort made to predict and reduce the amount of conflicting fragrances.

When customers buy premixed fragrances that are not custom made, they do not have a choice about their contents. They cannot adjust the fragrances to be more gender specific or gender neutral (i.e. unisex), adjust the tenacity, or concentrations. The customers also do not have the ability to create new fragrances for special occasions, seasons or holidays.

Currently, there is a need for a more accurate system for creating custom fragrances which is less subjective, takes into account the customer's desires, the time-changing aspects of the fragrance, and can save the parameters of each customer's unique scents.

SUMMARY

In one aspect, the invention relates to a method of creating a personalized custom fragrance for a customer by providing a 'Perfumer's Organ' of variable strength scent liquids and normal strength scent liquids, grouped by family and by volatility category; allowing the customer to select and place scent liquid on a blotter to smell the scents for a plurality of scent liquids;

having the customer select at least two scents from at least two different volatility categories that the customer would like to be in the custom fragrance;

allowing the customer to smell the mixture of all of the selected scents simultaneously;

allowing the customer to delete scents that they would no longer like to be part of custom fragrance;

allowing the customer to add scents to be part of the custom fragrance.

It also includes again providing the currently selected scents simultaneously to the customer to allow the customer to smell the mixture of all of the selected scents;

determining an amount of each selected variable potency scent liquid to use based upon a prestored scent table;

determining the total number of drops N to be used for the selected container;

determining the number of drops of all of the variable potency scent liquids to be added to the selected container;

subtracting the number of drops of the variable potency scent liquids intended to be used from the total number of drops for the selected container N to result in the remaining drops ($N_{remain}$);

determining the number of normal potency scents selected (n) and dividing the remaining drops ($N_{remain}$) by the number of normal potency scents selected (n) to result in the number of drops for each of the n normal potency scent liquids to add to the container; and mixing the determined amounts of each selected scent liquids with a filler material to result in the custom fragrance.

The current invention may also be described as a device for interacting with an employee and a customer to create custom fragrances having an input device for receiving scents selected by the customer;

a memory having a pre-stored "training data" being a plurality of equations of desired combinations of variable potency scents and normal potency scents each multiplied by scaling coefficients ($\alpha_i$) and compatibility coefficients ($\beta_i$); and a CPU coupled to the input device and the memory. The CPU having an internal executable program causing it to:
   read in the scents selected by the customer;
   read in the training data and to create scaling coefficients ($\alpha_i$) and a compatibility coefficients ($\beta_i$) that would minimize differences between these coefficients and corresponding coefficients of all equations in the training set;
   use the generalized equation with the created coefficients and the indication of the scents selected from the customer to define the volume of each scent to be mixed to create a desirable custom fragrance.

The invention may also be describe as a method of mixing fragrances from variable potency scents and normal potency scents selected by a customer comprising the steps of:

acquiring a scent table of variable potency scents indicating the volumes "$X_i$" of each variable potency scent "i" to use for several different sized containers to be used in creating the custom fragrance;

for each scent "i" where i=1 through n variable potency scents, looking up a volume $X_i$ in the scent table;

determine the total variable potency volume $X_T$ for all selected scents; adjusting the volume of each scent i by $$S*(X_i/X_T)*2.67=N_i$$

where $N_i$ is the number of drops for each variable potency scent "i", S=formula size (mL);

determining the remaining amount $N_{remain}$ to be filled with the normal potency scents;

acquiring a training set of general equations for highly desirable fragrances each indicating the relative amounts $N_i$ of each scent to use, wherein the equations have a volume coefficient and a compatibility coefficient for each of the scents;

fitting a generalized equation $N*Y*\Sigma(\alpha_i*\beta_i)=N$, to the training set of equations to determine the volume coefficients $\alpha_i$ and the compatibility coefficients $\beta_i$, where N=total drops in formula, Y=filling factor, $\alpha_i$=scaling coefficient for each scent in the formula, and $\beta_i$=compatibility coefficient for each normal potency scent in the formula;

using the equation $N*Y*\alpha_i*\beta_i=N_i$ to identify the number of drops of each normal potency scent to use in completing the custom fragrance.

BRIEF DESCRIPTION OF THE DRAWINGS

It will be appreciated that the illustrated boundaries of elements in the drawings represent only one example of the boundaries. One skilled in the art will appreciate that a single element may be designed as multiple elements or that multiple elements may be designed as a single element. An element shown as an internal feature may be implemented as an external feature and vice versa.

Further, in the accompanying drawings and description that follow, like parts are indicated throughout the drawings and description with the same reference numerals, respectively. The figures may not be drawn to scale and the proportions of certain parts have been exaggerated for convenience of illustration.

DETAILED DESCRIPTION OF A PREFERRED EMBODIMENT

Theory

In the current process, the customer decides the parameters of the fragrances.

For example, men typically gravitate to the scent families of earthy/woody, herbal, fresh and clean and citrus.

For tenacity, the customer 5 can decide how long the fragrance will remain by selecting higher or lower notes (higher and lower volatility scents). The fragrance concentration level can also be adjusted from EDP (eau de parfum) to EDT (eau de toilette).

Fragrances can also be created for a certain occasion such as a wedding day, date night, etc.

System & Method

Figure 1:
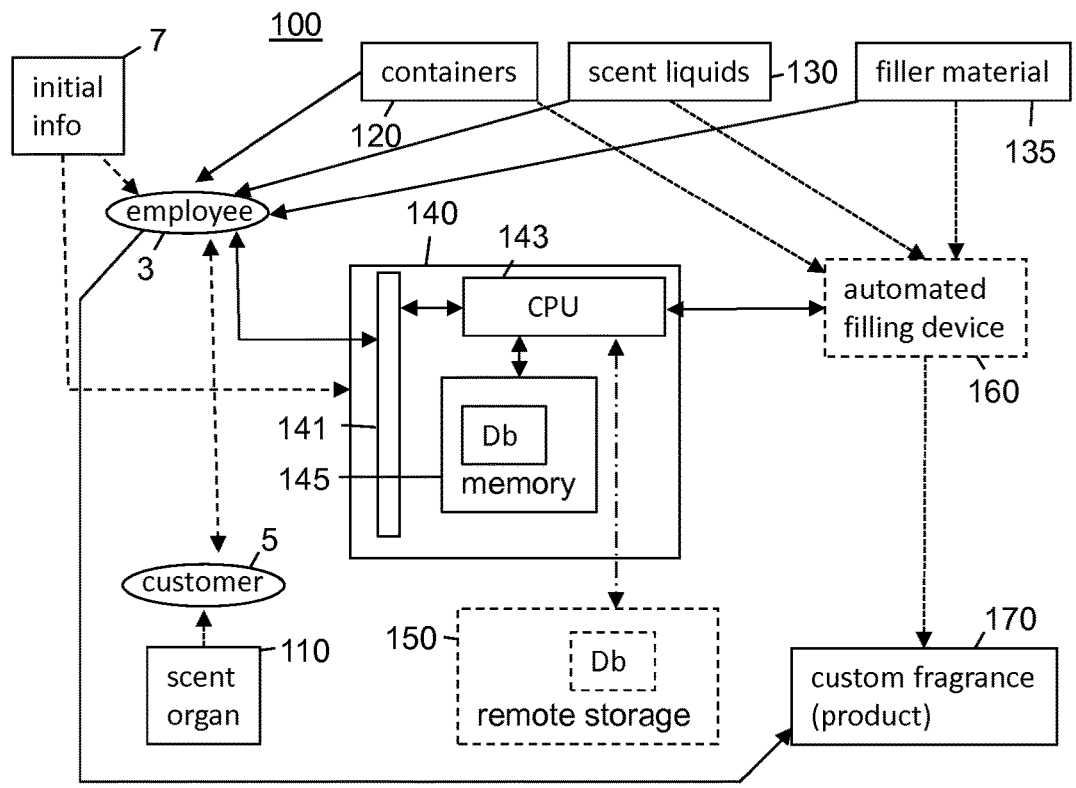
FIG. 1 is an overall block diagram of a custom fragrance creation system according to one embodiment of the present invention.
Figure 2:
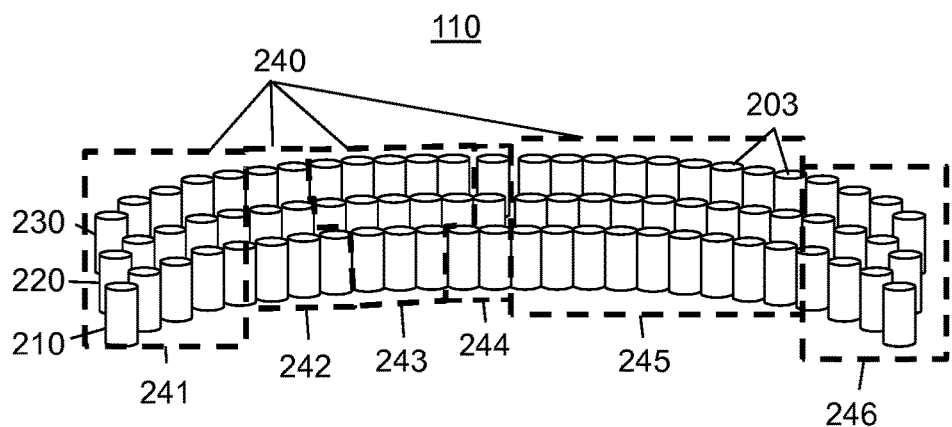
FIG. 2 is a 'Perfumer's Organ' showing one embodiment of scents arrangement according to the present invention.

FIG. 1 shows the overall custom fragrance system 100. A customer 5 visits a store having an employee 3. The employee 3 describes the process and directs the customer to a Perfumer's Organ 110 having a variety of scents grouped by molecular size, weight, tenacity and volatility and scent family (as shown in FIG. 2).

These scents may have normal potency or variable potency. The normal potency scents each have the same scent intensity when the same amount is used. (Larry-Also though, when a custom fragrance is blended, the potency of the individual scent may change depending on the levels used and/or the other scents in the formula.

However, the variable potency scents require varying amounts to produce the same scent intensity. These are experimentally determined and tabulated. These tables are pre-stored with other information in the initial information 7 of FIG. 1. There may be several entries in the tables for each variable potency scent relating to number of drops for various sized containers, various concentrations such as eau de toilette, and eau de parfum or for personal care products such as a body créme or bar soap. It may also include the total number of drops "N" to be used in a container size, as well as other information useful in calculating amounts of scents to be used.

The customer 5 interacts with the Perfumer's Organ 110 and the employee 3 to select various scents to be used to create a custom mixture of scents, also referred to as a custom fragrance.

The customer 5 determines the scents to be used in the mixture, the type of product, the container size and if a perfume or cologne or a personal care product, and the concentration level of aromatic compounds (eau de parfum, eau de toilette). The customer 5 provides this information to the employee 3.

In a first embodiment, the employee, referred to as a "Scent Designer" 3 determines which scents selected by the customer 5 are normal potency scents and which are variable potency scents. The employee 3 reads from a predefined table in a training manual referred to in FIG. 1 as the initial information 7, the number of drops for the selected container size for each of the variable potency scents for a given concentration, such as eau de parfum, eau de toilette, etc. The predefined tables are the result of experimental work determining the relative perceived strengths of various scents. The table entries are numbers of drops of each variable potency scent required for each variable strength scent to create a standard perceived scent intensity. There are different entries for different sized containers 120. The number of drops placed in the container 120 for all of the variable potency scents is subtracted from the total number of drops "N" to be placed into the container, to result in the total number of drops of normal potency scents.

The Scent Designer asks the customer their likes and dislikes, what scents they want to highlight or make any scents more pronounced than others (i.e. the customer 5 would like more lilac or want lilac to be the overall aroma of the fragrance). The opposite is also true in that if a customer wants to tone down a scent, only wants to smell a little bit of it, that can be done as well. The Scent Designer will incrementally increase or decrease the number of drops according to the customer's request.

Scent Designers 3 may adjust the formula based on how different scents react or perform with each other. For example, a customer 5 may say they want a large amount of patchouli in their formula. Patchouli is recommended at 8 drops in the 30 ml bottle. Since its strength is so overpowering of the other notes, the amount used must be within a predetermined range of the amount indicated in the scent table. For example, if the predetermined range is 10%, the maximum amount used would be no more than 110% of the amount in the scent table. For most cases, the predetermined range is 5%-15%.

This resulting number is evenly divided by the number "n" of normal potency scents. This is the number of drops "$N_i$" of each of the normal potency scents to be used.

A filler material which corresponds to the product selected by the customer is added to the container 120 leaving room for adjustment. For perfume and cologne products, the filler material is typically denatured alcohol.

In another embodiment, the employee 3 interacts with a computing device 140 to enter the customer's selections. The computing device 140, in this embodiment has an input-output device, such as a screen 141 for receiving input from the employee and for displaying information to the employee. It communicates information with a CPU 143. The CPU interacts with an internal memory 145 which may have a stored database, and optionally with a remote storage device 150 which also may have a stored database.

The CPU 143 employs the input provided by the employee 3 and initial information 7 from the training manual and stores them in the database(s). The CPU 143 determines the amount of each of the scents to be used in the custom fragrance.

In another embodiment, the employee 3 places the amounts of each of the scents indicated by the computing device 140 into the container 120 specified by the customer 5.

The employee 3 then also places the amount of the filler material in the container 120.

At this point the container is mixed and provided to the customer 5. The customer 5 then is allowed to provide feedback on which scents to increase or decrease. The employee 3 then adds an additional amount of the scent indicated to be increased. In the case where the customer 5 would like to decrease a scent in the mixture, then the employee 5 increases the amount of all other scents except the one that is intended to be decreased.

The customer 5 is allowed to smell the mixture and repeat the previous adjustment steps until they are satisfied.

The filler material 135 is then added to fill the container to result in the custom fragrance 170 which is the end product.

In an alternative embodiment, an automated filling device 160 is controlled by the computing device 140. The automated filling device 160 receives the container 120 selected by the customer 5, the filler material 135 corresponding to the selected product to be made and the calculated amount of each scent to be added to the container 120. This automatically prepares the custom fragrance interactively created by customer 5.

In an alternative embodiment, the current mixture is provided to the customer 5 to smell. The customer 5 indicates scents to increase and those to decrease. These are provided to the computing device 140 by the employee 3. The container 120 is inserted back into the automated filling device 160 and the computing device 140 adds scents to adjust the mixture according to the instructions from the customer 5.

FIG. 2 shows one embodiment of the Perfumer's Organ 110 having a number of scent oils, or scent liquids, which may be simply referred to as "scents" 203. These are bottles of different scents arranged in several different levels and partially wrap around the customer, as would a pipe organ. In this embodiment, there are three different levels, 210, 220 and 230. The scent liquids 203 on the lowest level 210 are the scents having the largest molecules and lowest volatility and highest tenacity, and referred to as the base notes. The scents on the middle level 220 are scents having mid-sized molecules, moderate tenacity and moderate volatility and are referred to as the middle notes. The scents on the upper level 230 are scents having small molecules with high volatility and low tenacity and are referred to as the top notes. These scents are grouped in scent families 240.

The embodiment of the Perfumer's Organ 110 shown in FIG. 2 has six scent families 241 through 246 which may be color coded. For example, one family may be the Citrus scents in yellow, such as lemon and orange. Herbals are in green, which include lavender, mints, and basil. Fresh and clean scents are in blue. Fruity, berry and tropical scents are in orange. Florals are in pink. Gourmand or edible notes are in tan, which include honey, vanilla and cinnamon. Earthy/woody notes are in brown. There may be many different embodiments of the Perfumer's Organ 110 that have various numbers of levels corresponding to the different volatilities and have various numbers of scent families 240.

Figure 3:
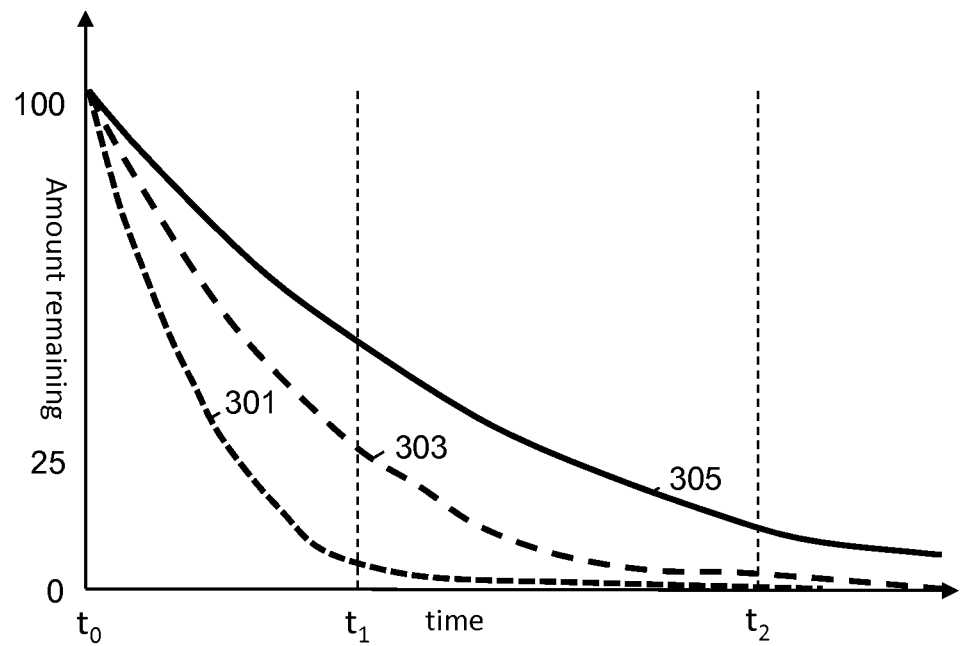
FIG. 3 is a graph of the remaining amounts of top, middle and base notes over time, showing the relative "tenacity" of the notes. Tenacity is defined as the ability of the fragrance to last on the skin and retain its characteristic odor.

FIG. 3 is a graphic representation showing the amount of three scents remaining over a period of time. In this graph, a scent that is a top note 301, a scent that is a middle note 303, and a scent that is a base note 305 each have the same perceived strength, or potency, are mixed in equal concentrations. Initially, at time $t_0$, the three scents are all at their maximum strength and equally contribute to the mixed fragrance.

However, since the top note 301 has the highest volatility, it quickly dissipates and loses the most of the original amount. Similarly, the middle note 303 has a reduced amount as compared with the base note 305. Therefore, at time $t_1$, the top note 301 is at about 5% of its original amount, the middle note 303 is at about 25% of its original amount and the base note 305 is at about 50% of its original amount. Therefore, at time $t_1$, the dominant scent is the base note 305. Middle note 303 contributes only half of the observable fragrance and the top note 301 is almost indistinguishable.

At time $t_2$, the fragrance perceived is almost entirely attributed to the bottom note 305. Therefore, by quantifying the strengths of the scents over time, the customer can select what a fragrance will be initially and what the fragrance will be at later times during the day. It is possible to select scents and notes to have a desired mixture, for example, at lunch time, or for a dinner party. Therefore, the employee educates the customer as to the time-changing nature of different notes and the customer takes this into account when selecting the scents and notes to be used.

In another embodiment, volatility curves, such as those shown in FIG. 3, can be used to develop a specific ratio of scents at a particular time of day. Therefore if a customer wants the fragrance to be 50% of scent 1, 25% of scent 2 and 25% of scent 3 at a noon luncheon, a mixture may be calculated that is applied at 7 am that results in this ratio of scents at noon. This can be done to extrapolate initial ratios, based upon the desired ratios at a later time.

Figure 4:
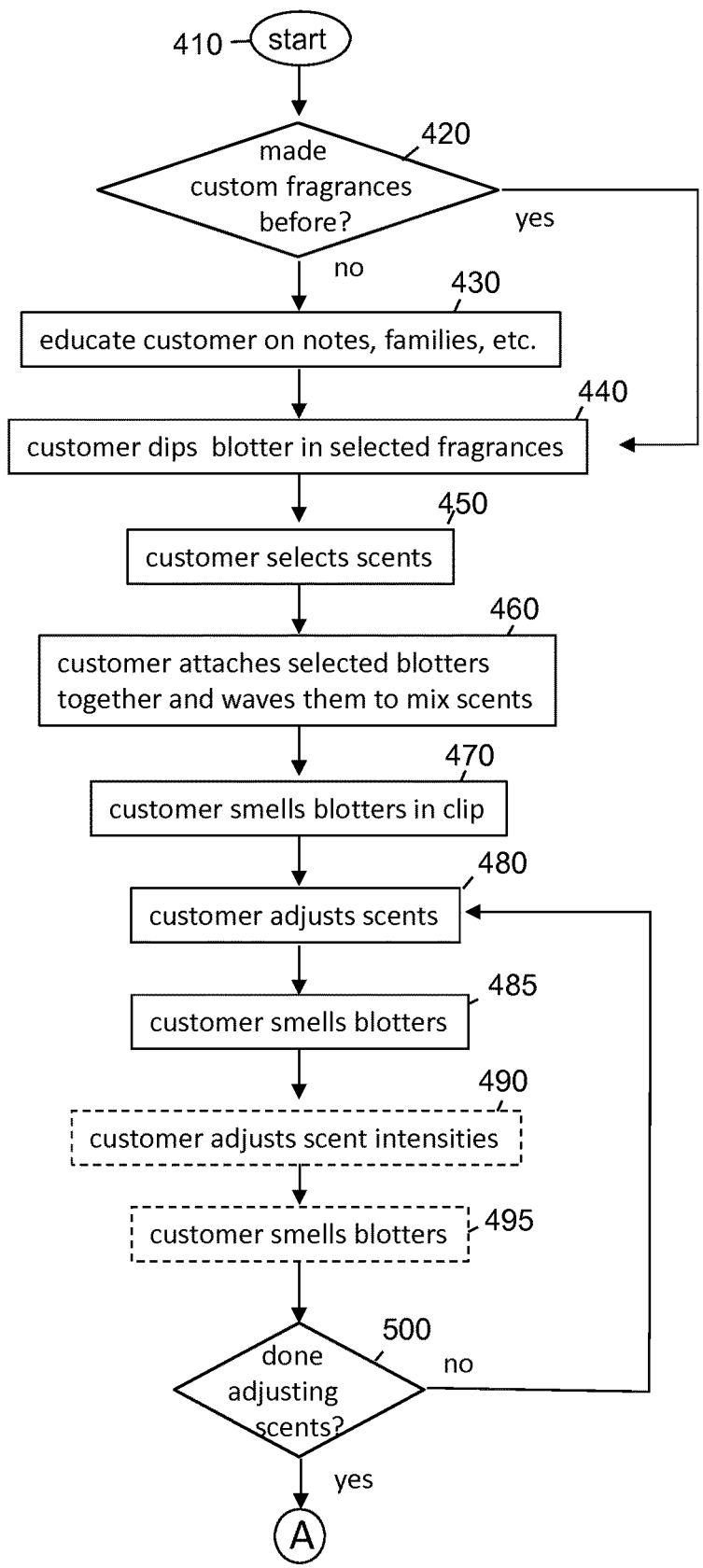
FIGS. 4, 5 and 6 together are a flowchart indicating the steps involved in the selection of scents and the creation of the custom fragrance.
Figure 5:
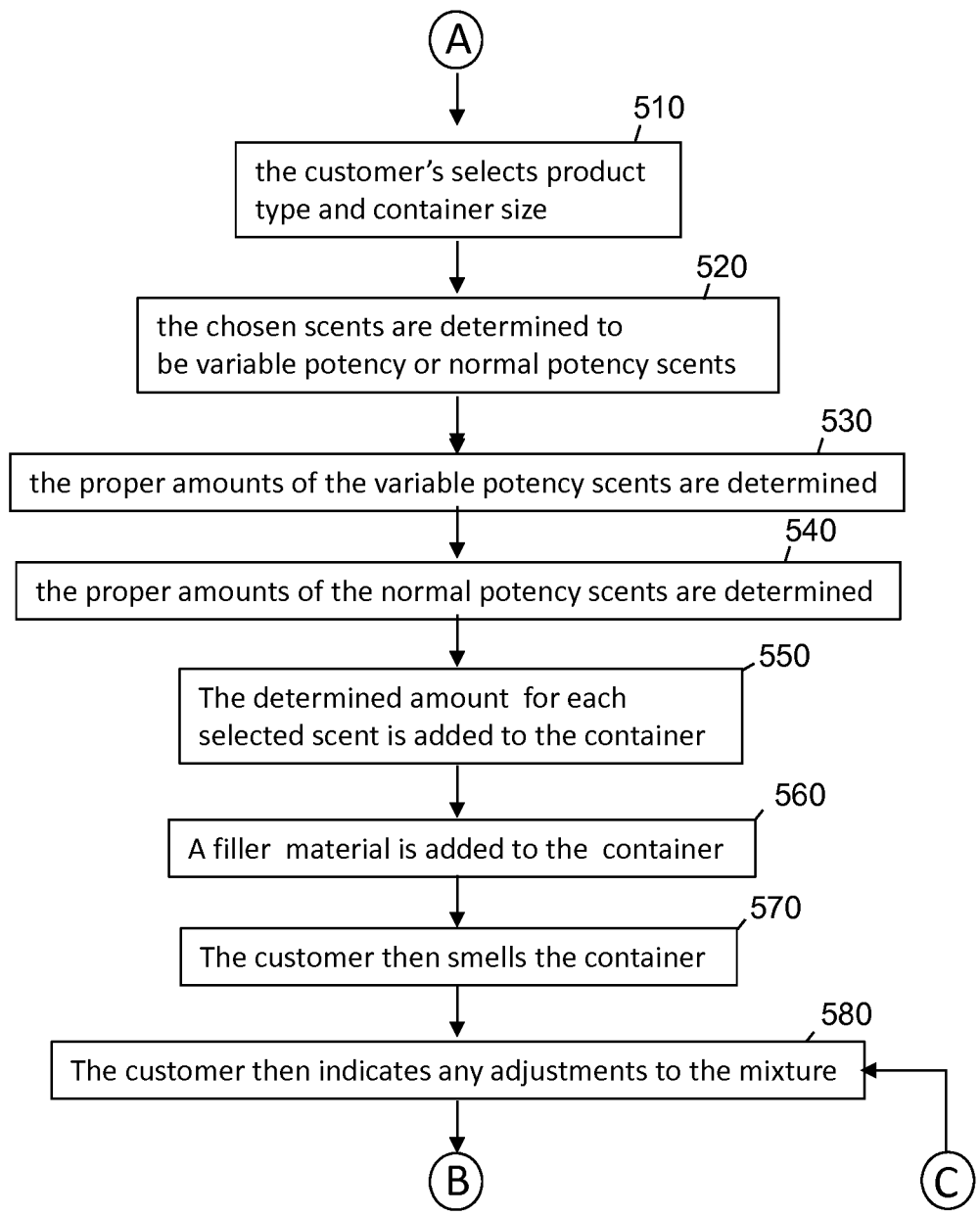
Figure 6:
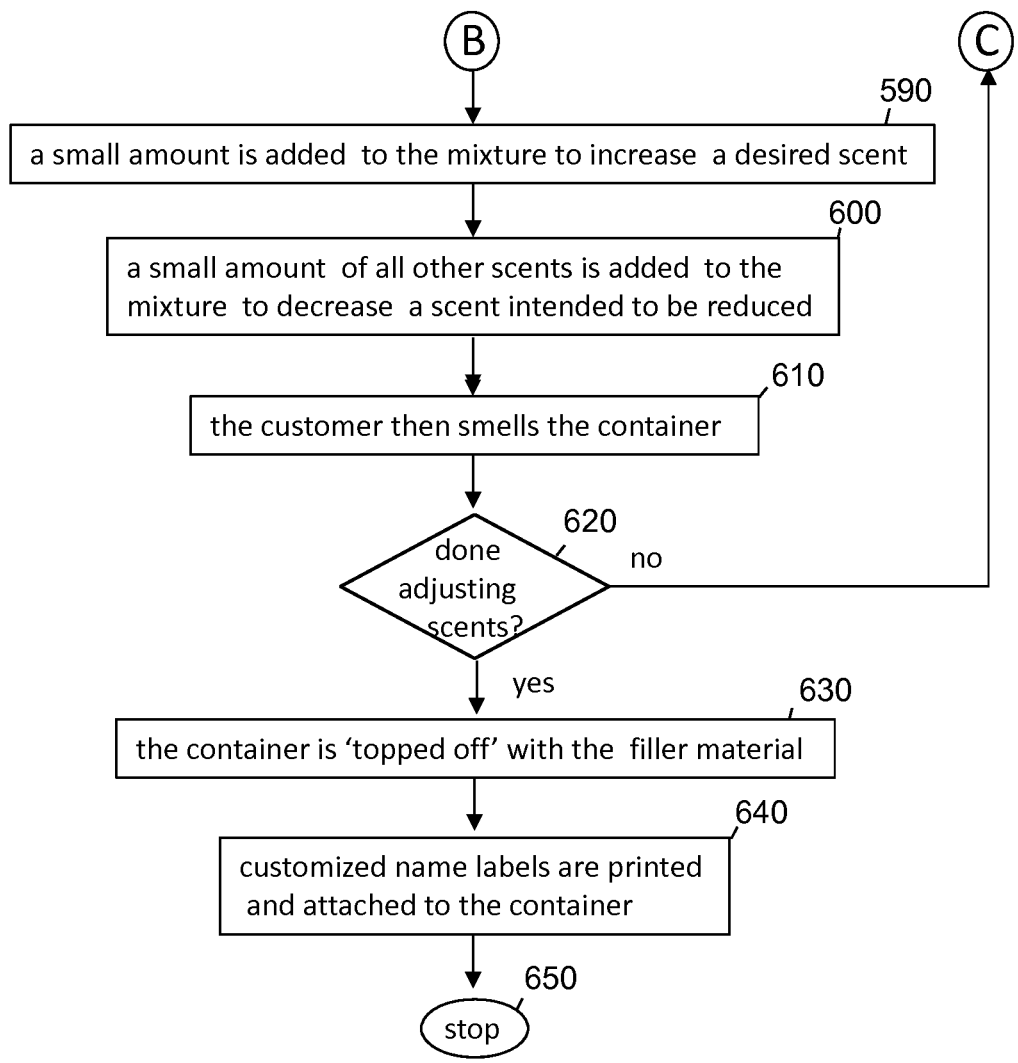

The process of creating custom fragrances can be embodied in the steps of the flowchart of FIGS. 4, 5, and 6.

The Employee Explains the Process

In order to create custom fragrances, there is some interaction between the employee and the customer. First the employee meets the customer and escorts the customer to a table which has the Perfumer's Organ.

In FIG. 4 the process starts at step 410. In step 420 the employee asks the customer if they had created custom fragrances before. If so, processing skips to step 440. If not, in step 430, the employee then educates the customer, explaining the Perfumer's Organ and how the scents are arranged by notes and by color-coded families.

The employee then indicates that when building a fragrance, it is best to have some top notes, some middle notes and some base notes in your blend. This helps to create a balanced and well-structured scent.

Next, the employee will show the customer the fragrance blotters that will be used to sample the scents and later blend the notes together. The blotters have a portion in which information may be written, such as the scent name. There is a portion which can be handled and a dipping portion which is dipped into a scent.

The Customer Chooses Initial/Subsequent Scents

In step 440, the customer would dip the blotter into a scent and smell the scent. If (s)he likes the scent, an identifying name is written on the blotter and the blotter is selected. The customer continues to select preferably 3 to 7 scents and preferably at least one scent for each note in step 450.

In step 460, all selected scents/blotters are attached together with the clip with the blotters slightly fanning out. The clip and blotters are waved through the air to mix the scents.

Sample with Clip and Blotters

The customer is then instructed to smell the mixed scents in step 470.

In step 480, the customer is allowed to adjust the scents chosen. This can be done by removing a blotter from the clip or adding another blotter with a different scent to the clip.

The customer then smells the adjusted scents in step 485.

Customer Adjusts Scent Intensities

In optional step 490, the customer can adjust the scent intensity. The scent intensity can be increased by adding blotters of the scent to be increased, selecting blotters of more surface area, or using blotters with higher absorbency to absorb more scent liquid, using marked blotters and dipping the blotters farther into the scent liquids, as indicated by the markings to result in more scent liquid on the blotter.

The scent intensity can be decreased by removing one or more blotters having the same scent, selecting blotters having less surface area, or using blotters with lower absorbency to absorb less scent liquid, or using marked blotters and dipping the blotters less of the distance into the scent liquids, as indicated by the markings to result in less scent liquid on the blotter.

Another way of reducing the strength of a scent would be to cut off a portion of the dipping end of the blotter having the scent oil.

The strength of a scent may also be reduced by limiting its interaction with the airstream as it is being waved. This may include folding the dipping portion of the blotter back upon itself, reducing the airflow over the dipping portion of the blotter, or shortening the blotter such that it spans a smaller arc when waved.

In step 495, the customer smells the blotters held by the clip and decides if they are done adding or deleting scents in step 500. If they are done, processing continues at step 510 of FIG. 5. If the customer is not done adjusting the scents, then processing continues at step 480.

In FIG. 5, step 510 the customer selects the product type, such as a perfume, cologne, lotion, soap, etc. The customer also selects the container size from several choices.

Scents Chosen by the Customer are Used to Create the Fragrance

The customer indicates the scents to use and the size of container and the concentration of the fragrance, if a perfume or cologne that (s)he desires. The fragrances may then be manufactured.

Manufacture of the Custom Fragrance Using a Table-based Method

In step 520, the scents are identified as either variable potency scents or normal potency scents.

Adding Variable Potency Scents

The variable potency scents provided in an equal amount do not provide equal impact upon the mixture. Therefore, there must be a table or equation indicating the amounts to use of each variable potency scent. The scents used in the Perfumer's Organ are listed below by name, classification, Family, color code in the Perfumer's Organ, Gender, Seasonality and Potency. The variable potency scents are indicated in the column marked "Potency":

| NAME | Class. | Family | Color Code | Gender | Seasonality | Potency |
|---|---|---|---|---|---|---|
| Black Amber | BASE | Earthy/Woody | Brown | feminine | Fall/Winter | Normal |
| Blue Musk | BASE | Earthy/Woody | Brown | feminine | Fall/Winter | Normal |
| Amber | BASE | Earthy/Woody | Brown | feminine | Spring/Summer | Normal |
| Driftwood | BASE | Earthy/Woody | Brown | masculine | Fall/Winter | Normal |
| Frankincense | BASE | Earthy/Woody | Brown | masculine | Fall/Winter | Variable |
| Leather | BASE | Earthy/Woody | Brown | masculine | Fall/Winter | Variable |
| Myrrh | BASE | Earthy/Woody | Brown | masculine | Fall/Winter | Variable |
| Patchouli | BASE | Earthy/Woody | Brown | Masculine | Fall/Winter | Variable |
| Sandalwood | BASE | Earthy/Woody | Brown | masculine | Fall/Winter | Normal |
| Sea Moss | BASE | Earthy/Woody | Brown | masculine | Fall/Winter | Normal |
| Almond | BASE | Gourmand | Tan | feminine | Fall/Winter | Variable |
| Buttercream | BASE | Gourmand | Tan | feminine | Fall/Winter | Variable |
| Chocolate | BASE | Gourmand | Tan | feminine | Fall/Winter | Variable |
| Honey | BASE | Gourmand | Tan | feminine | Fall/Winter | Variable |
| Vanilla | BASE | Gourmand | Tan | feminine | Fall/Winter | Normal |
| Lemongrass | MIDDLE | Citrus | Yellow | masculine | Spring/Summer | Variable |
| Carnation | MIDDLE | Floral | Pink | feminine | Fall/Winter | Variable |
| Neroli | MIDDLE | Floral | Pink | feminine | Fall/Winter | Variable |
| Ylang-Ylang | MIDDLE | Floral | Pink | feminine | Fall/Winter | Variable |
| Chamomile | MIDDLE | Floral | Pink | feminine | Spring/Summer | Variable |
| Frangipani | MIDDLE | Floral | Pink | feminine | Spring/Summer | Normal |
| Gardenia | MIDDLE | Floral | Pink | feminine | Spring/Summer | Variable |
| Jasmine | MIDDLE | Floral | Pink | feminine | Spring/Summer | Normal |
| Lilac | MIDDLE | Floral | Pink | feminine | Spring/Summer | Normal |
| Lily of the Valley | MIDDLE | Floral | Pink | feminine | Spring/Summer | Normal |
| Rose | MIDDLE | Floral | Pink | feminine | Spring/Summer | Normal |
| Tuberose | MIDDLE | Floral | Pink | feminine | Spring/Summer | Normal |
| Blackberry | MIDDLE | Fruity | Orange | feminine | Fall/Winter | Variable |
| Green Apple | MIDDLE | Fruity | Orange | feminine | Spring/Summer | Variable |
| Mango | MIDDLE | Fruity | Orange | feminine | Spring/Summer | Variable |
| Cinnamon | MIDDLE | Gourmand | Tan | masculine | Fall/Winter | Variable |
| Clary Sage | MIDDLE | Herbal | Green | masculine | Fall/Winter | Variable |
| Eucalyptus | MIDDLE | Herbal | Green | masculine | Fall/Winter | Variable |
| Sweet Basil | MIDDLE | Herbal | Green | masculine | Fall/Winter | Normal |
| Tomato Leaf | MIDDLE | Herbal | Green | masculine | Fall/Winter | Variable |
| Sweet Orange | TOP | Citrus | Yellow | feminine | Spring/Summer | Normal |
| Lime | TOP | Citrus | Yellow | masculine | Spring/Summer | Variable |
| Bergamot | TOP | Citrus | Yellow | Unisex | Spring/Summer | Normal |
| Lemon | TOP | Citrus | Yellow | Unisex | Spring/Summer | Normal |
| Pink Grapefruit | TOP | Citrus | Yellow | Unisex | Spring/Summer | Variable |
| Basmati Rice | TOP | Fresh & Clean | Blue | feminine | Fall/Winter | Normal |
| Cotton | TOP | Fresh & Clean | Blue | feminine | Spring/Summer | Normal |
| Green Tea | TOP | Fresh & Clean | Blue | feminine | Spring/Summer | Normal |
| Grass | TOP | Fresh & Clean | Blue | masculine | Spring/Summer | Normal |
| Ocean | TOP | Fresh & Clean | Blue | Unisex | Spring/Summer | Normal |
| Peach | TOP | Fruity | Orange | feminine | Spring/Summer | Variable |
| Raspberry | TOP | Fruity | Orange | feminine | Spring/Summer | Normal |
| Strawberry | TOP | Fruity | Orange | feminine | Spring/Summer | Normal |
| Lavender | TOP | Herbal | Green | feminine | Spring/Summer | Variable |
| Anise Star | TOP | Herbal | Green | masculine | Fall/Winter | Variable |
| Cream Mint | TOP | Herbal | Green | masculine | Fall/Winter | Variable |
| Peppermint | TOP | Herbal | Green | masculine | Fall/Winter | Variable |
| Spearmint | TOP | Herbal | Green | masculine | Fall/Winter | Variable |
| Sweet Bay Leaf | TOP | Herbal | Green | masculine | Fall/Winter | Normal |
| Coconut | TOP | Tropical/Fruity | Orange | feminine | Spring/Summer | Variable |
| Pineapple | TOP | Tropical/Fruity | Orange | feminine | Spring/Summer | Variable |

The amounts of the scents may be measured in terms of drops. "N" is the total number of drops of all scents in a container. "$N_i$" is the number of drops for a normal potency scent. "$X_i$" is the number of drops for variable potency scent "i". Therefore, in step 530 for an equal impact, or perceived fragrance strength, the number of drops for a given container size is found in the table and used. This is repeated for all variable potency scents. The total number of drops for the variable potency scents for "n" scents is $X=sum(X_i)$ from i=1-n.

Normal Potency Scents

The remaining number ($N_{remain}$) of normal potency scents drops to be added to a container of this size is $N_{remain}=N-X_t$ drops. These are added in equal proportions in step 540. Therefore, if $N_{remain}$=100 drops and there are 5 remaining normal potency scents, there would be 20 drops of each of the five remaining normal potency scents.

The amounts determined for each of the variable potency scents and the normal potency scents are added to the selected container in step 550.

Adding Filler Material

A carrier material is added to the variable potency scent drops and the normal potency scent drops in the container. For a perfume or cologne the carrier material may be an alcohol solution.

The overall perceived strength or concentration can be adjusted as per the request of the customer. Therefore, different entries will be listed in the initial information (7 of FIG. 1) for variable potency scents for different strengths of the fragrance. The normal potency scents will be all reduced by a similar proportion. This will adjust the overall strength of the fragrance. So if the customer requests something that is light in concentration levels, like an eau de toilette, the ratio of the number of drops of scent liquid to that of filler material can be adjusted to be approximately a level of 12-15%.

The concentration can also be adjusted based on the age of the customer. Customers aged 12 and under receive the eau de toilette concentration. The typical concentration for adults is an eau de parfum concentration level of 15-20%. In other embodiments, other concentration levels may also be offered.

For lotions, creams or other body care products the filler material may be a topical oil base, or may be a wax-based substance for other products. The container is then filled to about 80% of its capacity in step 560, leaving room for adjustment.

Customer Samples the Mixture

The customer is then allowed to smell the mixture in step 570 and provides feedback in step 580.

Adjusting Upward or Downward

In FIG. 6, the customer may indicate that (s)he would like more of a certain scent. In such case several additional drops would be added to the mixture in step 590.

If the customer would like to have a certain scent diminished, then a few drops of all other scents in the mixture will be added in step 600.

In step 610 the customer smells the adjusted mixture.

In step 620 the customer determines if the adjustment is finished. If so, processing continues at step 630.

If further adjustments are required, then steps 580 through 620 are repeated until the customer is satisfied with the mixture. Once the adjustments are completed, the information is recorded with a unique ID number. Every customer receives a unique ID number for every formula created. This is done for identification and categorization of formulas and reordering purposes. The customer receives a key tag with their ID number on it to simplify the reordering process. This information may also be stored in the computing device 140 and used for various purposes and analyses. For example, the most popular scents may be determined, the most common combinations, etc. This may also be used for inventory and restocking of scent materials. Finally, these may be used for advertising, marketing and consumer research purposes.

In step 630, the mixture is topped off with the filler material.

Since the customer has created the personalized fragrance, they may name the fragrance. In step 640, personalized scent name labels are printed with the name the customer has chosen and the personalized labels are affixed to the finished product. This adds another level of customization and personalization. The process is completed in step 650.

Figure 7:
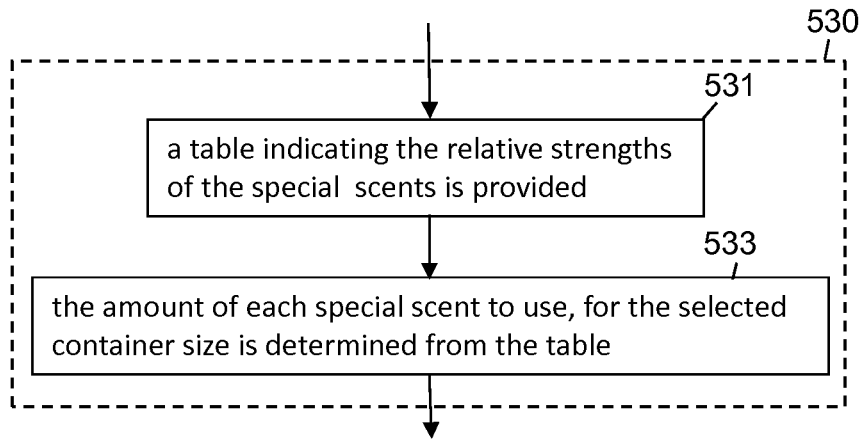
FIG. 7 is a more detailed flowchart of the step of determining amounts of variable potency scents to be used in the custom fragrance.

FIG. 7 illustrates the steps of one embodiment for determining the proper amounts of variable potency scents of step 530. In step 531, the scent table of the initial information (7 of FIG. 1) is input to the system. The amount of each variable potency scent for the selected container size and desired concentration is taken from the scent table and used.

Figure 8:
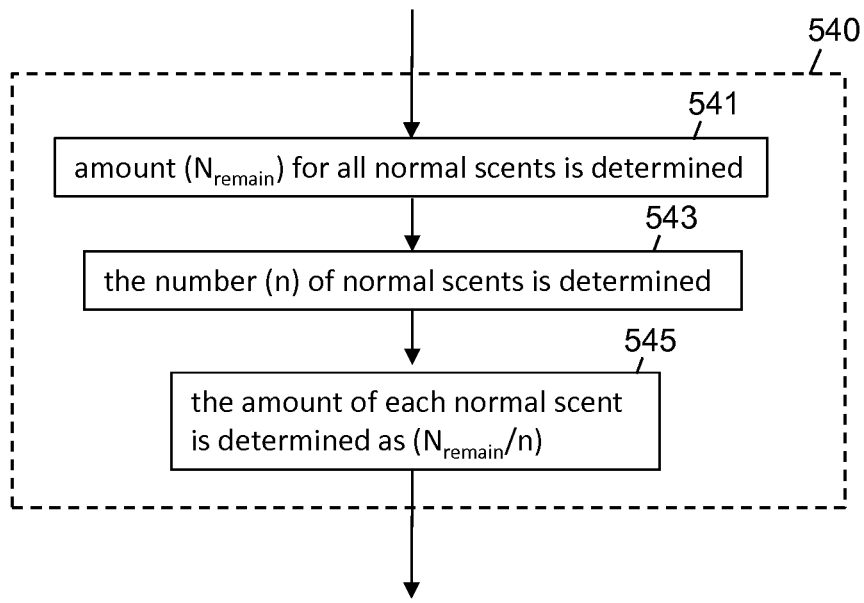
FIG. 8 is a more detailed flowchart of the step of determining amounts of normal potency scents to be used in the custom fragrance.

FIG. 8 illustrates the steps of one embodiment for determining the proper amounts of normal potency scents of step 540. In step 541, "N" is taken from the tables in the initial information (7 of FIG. 1) for a given container size. The amount of variable potency scents is subtracted from the total number of drops to be used "N" to result in the remaining amount "$N_{remain}$" for all of the normal potency scents.

In step 543, the number "n" of normal potency scents is determined.

In step 545, the amount for all of the normal potency scents "$N_{remain}$" is divided equally for the "n" normal potency scents in the mixture.

Figure 9:
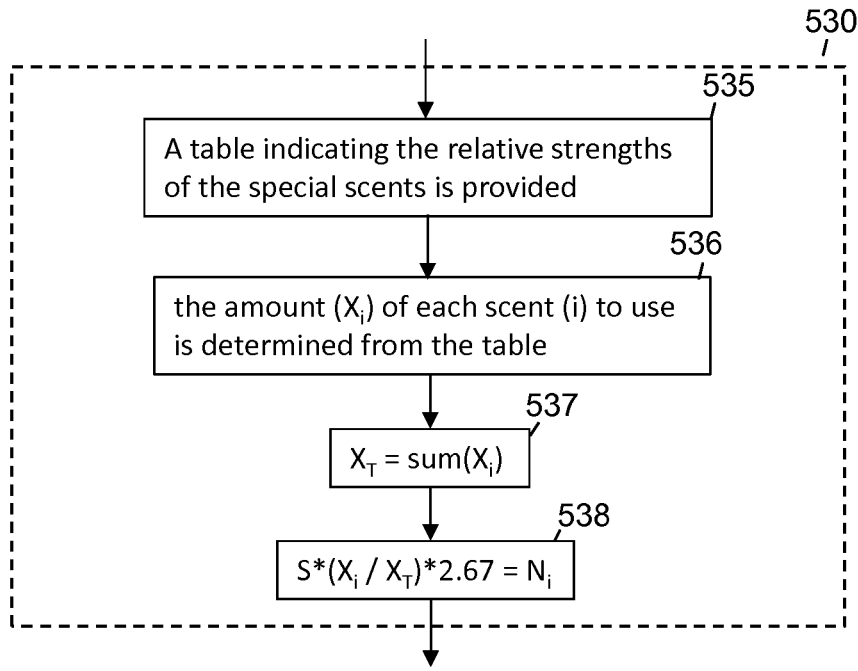
FIG. 9 is a more detailed flowchart of another embodiment of the step of determining amounts of variable potency scents to be used in the custom fragrance.

FIG. 9 discloses a slightly different embodiment for determining the variable potency scents amounts from that of FIG. 7. In step 535, a scent table is provided, however this one is not adjusted for container size.

In step 536, the amount for a standard volume of each scent $X_i$ to use is taken from the table.

In step 537 all of the "$X_i$" are summed to get the total $X_T$.

In step 538, the ratio of "$X_i/X_T$" is adjusted for the container size "S" and a constant to result in the number of drops of each variable potency scent "$N_i$".

Formula Prediction Algorithm

In an alternative embodiment, the manufacturing of a pleasant fragrance incorporates the following computations.

All of the scents are identified by an identifier number "i". A number of formulas or mixtures which have had significant success are selected and are referred to as the "training set" or the "training data". Each mixture is a combination of the amounts of at least two of these scents. (It is possible for the amount of one or more scents in the training data to be zero or near zero.)

The intent is to take a generalized equation (1) and to iteratively adjust the coefficients $\alpha_i$ and $\beta_i$ to fit it to the training data.

Modeling of Perfume Formulas

The composition of any given perfume formula is modeled by the following equation:

$$N*Y*[(\alpha_1*\beta_1)+(\alpha_2*\beta_2)+(\alpha_3*\beta_3)\ldots+(\alpha_n*\beta_n)]=N \qquad \text{Eq. (1)}$$

for the n scent oils chosen by the customer. Equation 1 may also be written in another form as:

General Equation $$N*Y*\sum(\alpha_i*\beta_i)=N \qquad \text{Equation (1)}$$

N = total drops in formula
Y = filling factor
$\alpha_i$ = scaling coefficient for each scent in formula
$\beta_i$ = compatibility coefficient for each scent in formula Equation (1): General Equation The filling factor "Y" is the percentage that the chosen container is filled, allowing extra room for additional adjustments.

There are a number of known algorithms that fit a generalized equation to a set of training data (or training equations). Stochastic algorithms are uniquely suited for this problem because they can search a very large solution space with no prior domain knowledge. Preferably, a Stochastic algorithm is used which will introduce small, random changes in the variables being searched and keep those variable values that are beneficial.

The process starts with initializing $\alpha_i$ and $\beta_i$ to "1". Plugging these into Equation (2) results in a predicted set of the number of drops of each scent ($N_i$). The predicted set is then compared to the number of drops for all mixtures in the training set. The difference between the number of drops for the predicted formula and the first training mixture is calculated. This is repeated for all scents for all formulas in the training set. The total error is accumulated and the average of all of these errors is calculated.

Next, $\alpha_i$ is changed slightly and the process repeated. This is done iteratively until the change in error is below a predefined threshold. This indicates that the equation is converging to an answer.

Once this point is met, then the other coefficient $\beta_i$ is changed and the process repeated for coefficient $\beta_i$. This is done iteratively until the change in error is below a predefined threshold, indicating that it is converging to an answer.

At this point, $\alpha_i$ and $\beta_i$ are now defined and can be used in Equation (1).

Since the result is expressed in drops of each scent, it must be normalized for various sized containers using N, the total number of drops in a container and "Y" a filling factor.

N, the total drops, is determined by the formula size in milliliters. The standard values at each size can be found in the training manual which is the same as the initial information (7 of FIG. 1), but this algorithm predicts total drop counts at less than the recommended level to allow for adjustment. Currently, N=the size (mL)*3.83, a constant indicating the number of drops per milliliter for normal potency scents.

N, $\alpha_i$ and $\beta_i$ are now known, so the only free variable is Y, the filling factor. The filling factor guarantees that the sum of drops for individual scents is equal to the desired total drops, regardless of the number of ingredients in the formula.

General Equation (1) can be converted into Equation (2) which is specific for each scent.

Drops for each scent.

$$N*Y*\alpha_i*\beta_i = N_i \qquad \text{Equation 2}$$
$$N_i = \text{drops for each scent}$$

Equation 2: Drops for each scent.
Input
  Below is a list of input provided to the program.
  list of scents to be included in formula (from the user)
  formula size (bottle size in milliliters)
  resources
    variable potency scent table
    optimized solution (alpha and beta values),
Output
  new formula with the specified ingredients and size
  Using the inputs above and Equation (2), a new mixture is produced using the inputs from the user listed above to produce a desirable mixture similar to the list of scents provided by the user.
Derivation
  The derivation of this Eq. (1) is clarified by considering a formula where each scent is distributed in constant proportion: the equation would be $N*\Sigma(X_i)=N$, where $X_i$ is the proportion for each scent. To get Eq. (1), we make the proportion the product of two coefficients ($\alpha_{\square}, \beta_{\square}$) and the free variable Y. The filling factor Y allows us to guarantee that the formula contains the desired number of total drops and lets us specify an arbitrary range for alpha and beta.

Both alpha ($\alpha_i$) and beta ($\beta_i$) are the coefficients and are calculated by the optimization algorithm. $\alpha_i$ is a scaling coefficient for each scent that theoretically represents relative strength. $\beta_i$ is a compatibility coefficient that represents how well a given scent scales with the other scents in the formula. $\beta_i$ is the average of the beta values for the other scents in the formula. For example, in a formula with 5 scents the $\beta_i$ for each scent would be the average of the beta values for the other 4 scents.

It should be noted that the compatibility coefficient of scent A with scent B (for any two scents A and B) is not the same value as the compatibility of scent B with scent A. In other words, each scent possesses as many compatibility coefficients as there are other scents in the system.

For variable potency scents only.

$$S*(X_i/X_T)*2.67 = N_i \text{ and } S*2.67 = N \qquad \text{Equation 3}$$
$$S = \text{formula size (mL)}$$
$$X_i = \text{drops per mL for a given scent}$$
$$X_T = \text{the sum of } X_i\text{'s in the formula}$$
$$N_i = \text{drops for scent } i$$

Equation 3: For variable potency scents only.

Equation 3 is for variable potency scents only. These are scents that typically dominate over other scents, so their amounts (drops) used must be adjusted. When a formula contains only variable potency scents, the number of drops for each scent is scaled up from the recommended values so that the total drop count is not extremely low. Since there are approximately 2.67 drops per ml, the total number of drops for a formula that contains only variable potency scents is simply size in mL*2.67, where 2.67 is a constant specified by the client. The $X_i$ values are derived from a variable potency scent table which indicates the relative amounts of scents to be used based upon their inherent odor strengths. Tables of the initial information (7 of FIG. 1) of the variable potency scents are previously calculated. These may be calculated by experimentation to determine the amounts of each which provide a given strength. The resulting values are pre-stored in the training manual and in the initial information (7 of FIG. 1).

Summary of Automated Procedure

Below are the steps of one procedure for creating custom fragrances from the customer scent selections, and container size according to one embodiment of the present invention.

1.) Calculate the total drops (N) for the formula size with the following equation:

Total drops=formula size (mL)*number of drops/mL

This results in a filling factor of 87.5% of the recommended size, leaving room for adjustment.

2.) Calculate the number of drops for each variable potency scent "i" according to Eq. (3). As in the previous step, the number of drops for each variable potency scent is the product of the formula size in milliliters and the drops per milliliter for that scent (from the variable potency scent table).

3.) Calculate the in-formula compatibility value for each scent (beta) as the average of that scent's compatibility factors with the other scents in the formula.

$$\beta_i = \beta_k/(\text{\# of scents in formula}-1) \qquad \text{Eq. (4)}$$

4.) Adjust current scaling factors ($\alpha$) by the value of the compatibility factor ($\beta$) to result in a new scaling factor ($\alpha$).

$$\text{new } \alpha = \text{current } \alpha*\beta \qquad \text{Eq. (5)}$$

5.) Use the equation in Section "5b" below for formulas with variable potency scents, and the equation in section "6" below for formulas with normal potency scents.

5a.) Calculate the filling factor, Y with the following equation. The rationale for this calculation is more apparent in the full equation to the right. See the formula equation section for more details.

$$Y = 1 / \text{the sum of adjusted } \alpha\text{'s} \quad \text{Eq. (6)}$$

$$Y = N / \left( N * \sum (\alpha_i * \beta_i) \right)$$

5b.) Calculate the number of drops for each variable potency scent based on the Equation (3).

$$S * (X_i / X_T) * 2.67 = N_i \text{ and } S * 2.67 = N$$

$S$ = formula size (mL)

$X_i$ = drops per mL for a given scent $X_T$ = the sum of $X_i$'s in the formula $N_i$ = drops for scent $i$ 6.) Calculate the drops for normal potency scents based on the Equation (2).

$$N * Y * \alpha_i * \beta_i = N_i$$

$N_i$ = drops for each scent

"Y" is defined in Eq. (6), $\alpha_i$ is defined in Eq. (5) and $\beta_i$ is defined in Eq. (4).

Add all scents to formula and return completed formula.

6b. Empirical Method of Manufacture

6b1. Acquire Input Data

Figure 10:
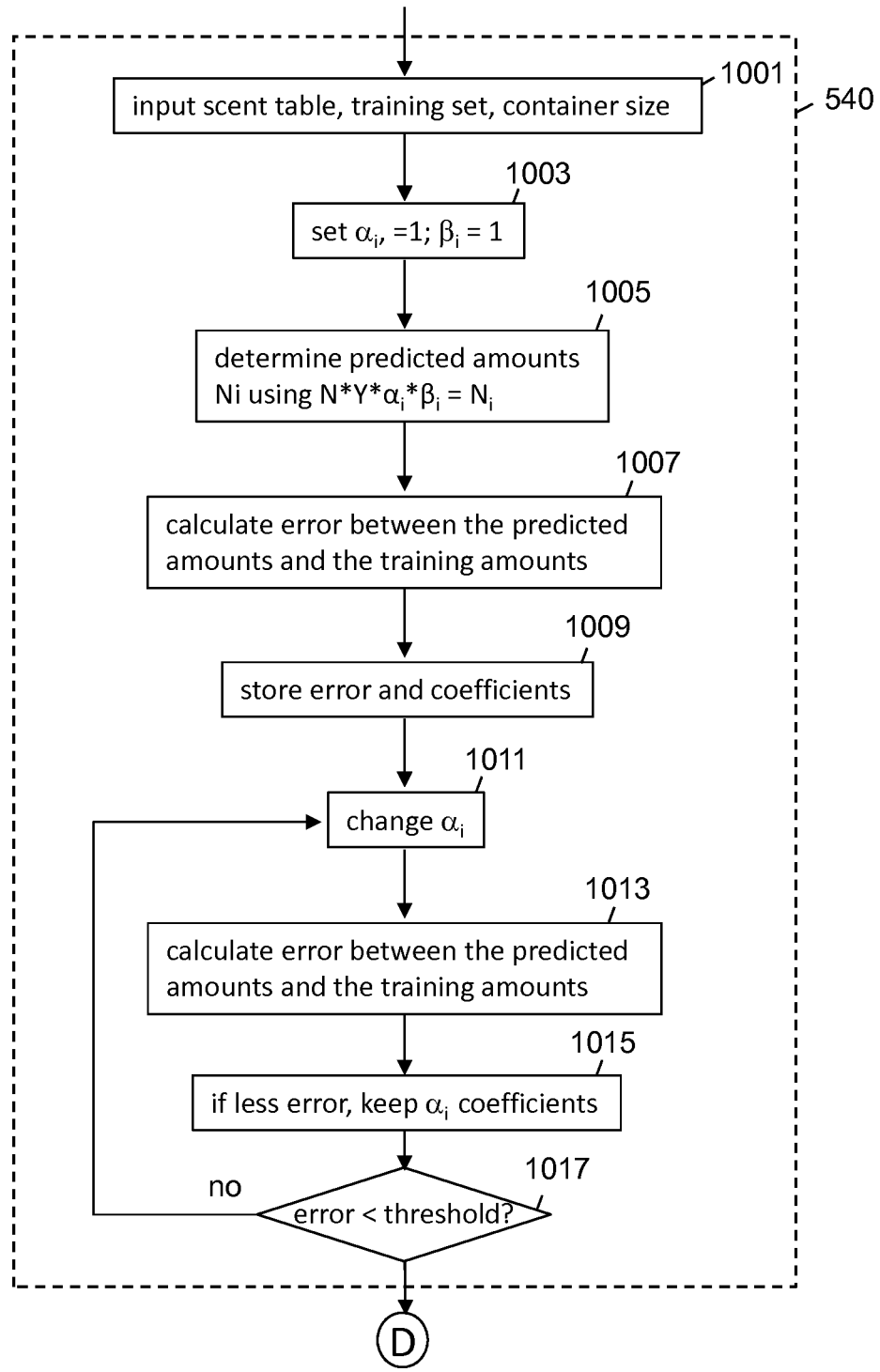
FIGS. 10 and 11 together represent a more detailed flowchart of another embodiment of the step of determining amounts of normal potency scents to be used in the custom fragrance.

In FIG. 10, step 1001, the variable potency scent tables are provided to a computing device (140 of FIG. 1).

A listing of scents and amounts of the scents that have been successful in the past, referred to as "training data" is also input to the computing device, in the same step.

The desired container size is identified and the type of product desired. Optionally, the type of product may be a perfume, cologne, a lotion, soap, etc. may also be input in this step.

In step 1003, a general equation Eq. (1) is initiated with alphas and betas="1".

In step 1005 the predicted amount of each scent is determined from general Eq. (1) for all scents.

An error is calculated in step 1007 between the predicted amount and the training data amount for the same scent. This error is summed for all equations of the training data and is used to determine a total error, and an average error that are stored in step 1009.

The alpha coefficients ($\alpha_i$) are slightly changed in step 1011 and the error is calculated as indicated for step 1007 in step 1013. If the average error is lower than the previously smallest average error to this point, it is stored with the coefficients with $\alpha_i$ in step 1015.

Figure 11:
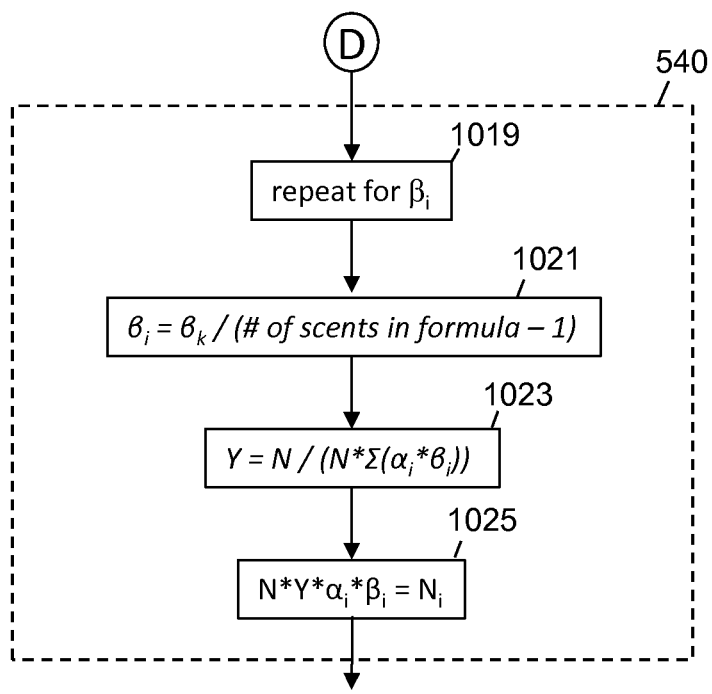

In step 1017, if the change in average error for the current iteration is less than that of the previous iteration, then the answer is converging and processing then continues at step 1019 of FIG. 11.

If the error in step 1017 is not less than the predetermined threshold, there should be more iterations and processing from steps 1011 through 1017 are repeated.

Repeat for Beta Coefficients

The process continues at step 1019 of FIG. 11. Steps similar to steps 1005 through 1017 are repeated but by varying $\beta_i$ instead of $\alpha_i$.

In step 1021, $\beta_i$ is calculated.

The Filling Factor is Determined.

In step 1023, the filling factor "Y" can now be determined, since "N", "$\alpha_i$," and "$\beta_i$" are now known.

Determining the Amounts of Scents

Plugging in the $\alpha_i$, $\beta_i$, and user scent choices into Eq. (3) results in amounts of each scent to put into the selected container. Finally, the drops "$N_i$" of the normal potency scents "i" can be determined in step 1025.

The 'hill climbing algorithm' is one algorithm that may be used to determine these alpha and beta coefficients for the general equation. There are other commonly known algorithms which also may be used to fit the generalized Eq. (1) to a set of training data.

Software Implementation

The software implementation of a portion of the system determines perfume formula composition. In addition, it acts as a store management tool. The system algorithmically optimizes a set of formula composition variables based on previous formulas. Information about formulas, orders, customers, and employees is stored in a database (currently implemented in MySQL), which can be edited through an interface provided to administrative users.

The system is designed to predict how to create a fragrance (mixture of scents) based on previous ones, even for combinations of ingredients that were never used. This "prediction engine" must work in the context of a larger application which will have additional functions.

Overview

Referring to FIG. 1, a computing portion of the system according to one embodiment of the current invention has three main components: the prediction algorithm running in the CPU (143 of FIG. 1), a MySQL database (which can be in local memory 145 or in remote storage 150, both of FIG. 1), and the graphical application operating user interface (141 of FIG. 1) through which the client will interface with the other two components. The graphical component has been developed with Java Swing. It will provide the ability to edit the database, compose new formulas, and view the most-used ingredients. Predicted formulas will be adjustable for customer satisfaction before being finalized.

The first stage of the prediction algorithm was built with a "naive" approach. Roughly speaking, the table prescribes equal proportions for all normal potency scents except for variable potency scents. Employees are expected to develop a sense of composition beyond the simple guidelines in the manual. The first prediction algorithm merely implements the manual guidelines, as an employee on day-one would be expected to do, without any experience-based intelligence. Since the ultimate goal of the prediction algorithm is to incorporate data from previous successful formulas into future ones, the naive algorithm will likely only be used for comparison purposes.

The problem of algorithmic formula composition is fundamentally a parameter optimization task. The structure of the data makes it difficult to come up with a meaningful experimental design, however. Each formula is a piece of categorical data which contains any number of other categorical items (ingredients). The parameter that must be optimized is a numerical quantity associated with each ingredient. The standard technique of dummy-encoding categorical variables might impose an arbitrary and incorrect ordering. For this reason, a standard statistical analysis is not being used.

The second iteration of the prediction algorithm uses a stochastic optimization algorithm. Stochastic algorithms introduce small, random changes and keep those that are beneficial. Stochastic algorithms are uniquely suited for this problem because they can search a very large solution space with no prior domain knowledge. This is important because there is no mathematical procedure for codifying intuition. We can express a formula as a set of parameters, however, and maximize the degree of similarity between predicted and actual formulas. The parameters being optimized are a scaling factor associated with each scent and a compatibility factor between scents.

Justification

It is believed that there have not been any previous attempts at algorithmic perfume formula composition, so there is no status quo by which to compare the performance of the system.

The prediction algorithms work by incrementally minimizing the average percent error between predicted formulas and formulas in the training set.

The system functions to eliminate the need for each employee to learn how to manufacture the custom fragrances.

System Model

Figure 12:
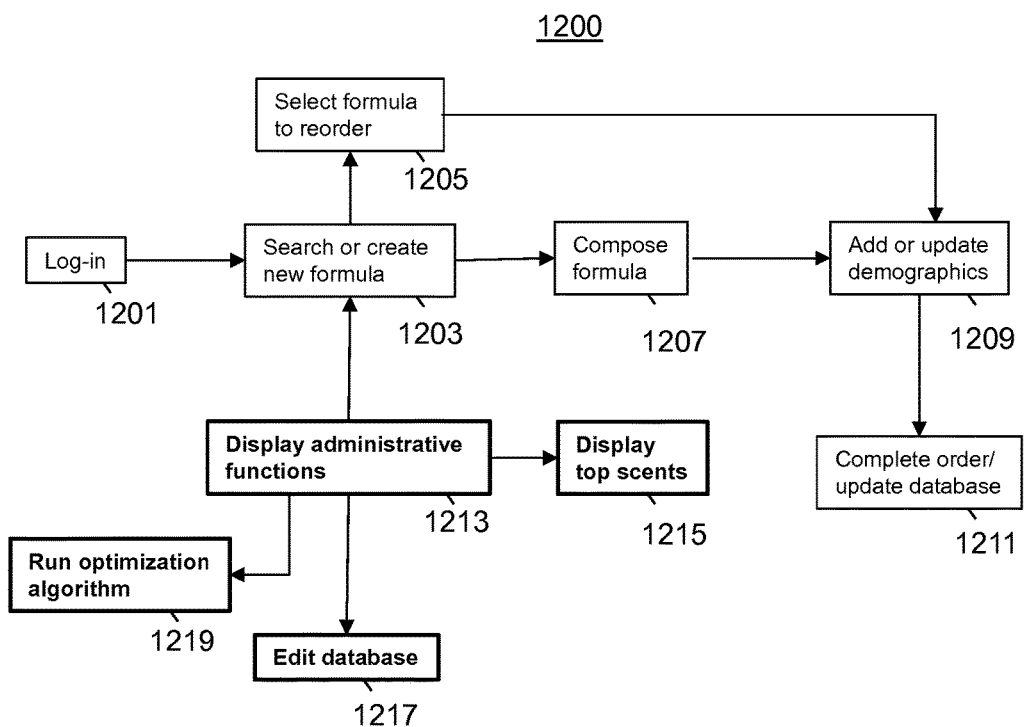
FIG. 12 is a schematic block diagram showing the functional blocks of the software subsystem according to the present invention.

FIG. 12 shows the major functional blocks of the software portion 1200 of the system. After a user logs in to the system in block 1201, the user will have to indicate if (s)he is either a) an employee or b) an administrator.

Employees will have access to the formula composition interface 1207. They will also be allowed to search for previous formulas in block 1205 by the formula ID or the owner's last name, compose formulas, and collect demographic information from the customer in block 1209. At the end of this process, the information will be uploaded to the database in block 1211.

Administrators will be able to access all of the employee functions described above, as well as those blocks having boldface text in FIG. 12. These include editing the contents of the database in block 1217 and viewing the most used scents in block 1215, among other common administrative functions.

Functional Requirements

Employees

One benefit of this system for employees is the streamlining of the customer service process. As shown in the system model of FIG. 12, a software subsystem 1200 will guide employees from the beginning to the end of an order. After the employee logs in in step 1201, the next step, 1203, allows the employee to select creating a new formula or reordering a formula that was previously created.

If the customer is reordering in step 1205, the employee may navigate to the desired formula by either searching for the customer's last name or by directly inputting an identification number associated with that formula. When searching by name, the application will display all of the formulas created by that customer and allow the employee to choose one.

When creating a new formula in block 1207, the employee will input the scents selected by the customer to be included and the software subsystem 1200 will automatically generate a composition based on previous formulas. The employee can then adjust the amount of each scent based on customer preference before moving on to the final step.

Once a formula has been created or selected, the employee will enter the customer's demographic information; this includes name, address, birthday, customer notes, and a formula name if the customer so chooses in block 1209. The subsystem 1200 will ask for confirmation before updating the database; at any point before this step, the user can go back to a previous step to make changes.

Administrators

Administrators must have access to the same functions as employees, but also have additional functional abilities which are prompted to the Administrator in block 1213. These allow the Administrator the ability to directly interact with the database in block 1217. They will be able to select from four broad categories of data:

employee information,
customer information collected in the demographic section,
formula information, and
scent information.

The administrator will be able to add, delete, or update entries in each of these categories.

It is also the administrator's responsibility to run the prediction algorithm in block 1219 which determines the alpha and beta coefficients for the generalized equation. The prediction algorithm is also run after adding new formulas to the training set. The algorithm will automatically terminate once it detects that improvements are no longer significant, or can be manually stopped when desired.

The administrator has the ability to search, view and display the scents most often included in customer formulas in block 1215. Various other search criteria may also be used.

User Interface Specification

Each block in the system model corresponds to a different screen and sub-task in the application:

Demographics—the user types customer information into a set of text boxes in block 1209.
Optimization—displays the current percent error and time elapsed and can be halted with stop button
Search—the user specifies whether they are searching by last name or I.D. with a drop-down menu and types their query into the associated text box.
Search results—if search is by last name, displays all of the owner's formulas in step 1203. User selects one with radio button, or other conventional means. If search is by I.D., it then displays the formula.
Top scents—displays scent names in order of most to least used in block 1215. Select all-time or month with radio button. The Administrator can select month and year from dropdown menu.

Formula Composition Interface

When creating a new formula in block 1207, the user will first be presented with a tabbed menu of scents.

There will be at least three tabs (top, middle, and base) representing one of the many ways in which scents can be categorized; these particular categories correspond to scent molecular weight and the length of time a scent remains detectable after being applied. Typically, a balanced formula contains at least one scent from each category. Scents chosen by the customer will be selected on the screen by the employee via check boxes and the user will then proceed to the adjustment screen.

The adjustment screen will display the algorithmically generated drop count for each scent selected in the previous step. The user can modify these numbers up or down via arrow buttons or can directly change the value by typing inside the text box that displays the drop count.

Database Modification Interface

In block 1217, the employee will select one of the four information types (employee, customer, formula, or scent) from a drop-down menu. The screen will then display the database contents for that category in the form of a spreadsheet-like grid of text boxes. The employee can add a new entry by clicking the "add" button, or delete entries by selecting a checkbox at the beginning of each row and clicking a "delete" button. When the user is done editing, they will click the "save" button to update the database.

While the present disclosure illustrates various aspects of the present teachings, and while these aspects have been described in some detail, it is not the intention of the applicant to restrict or in any way limit the scope of the claimed systems and methods to such detail. Additional advantages and modifications will readily appear to those skilled in the art. Therefore, the teachings of the present application, in its broader aspects, are not limited to the specific details and illustrative examples shown and described. Accordingly, departures may be made from such details without departing from the spirit or scope of the teachings of the present application. Moreover, the foregoing aspects are illustrative, and no single feature or element is essential to all possible combinations that may be claimed in this or a later application.

What is claimed is:

1. A method of creating a mixture of scented liquids which has a personalized custom fragrance for a customer comprising the steps of:
   a) providing a 'Perfumer's Organ' of variable potency scent liquids and normal strength scent liquids, grouped by family and by volatility category;
   b) selecting a container of known volume;
   c) selecting at least two scents from at least two different volatility categories that the customer would like to be in the custom fragrance;
   d) selecting a blotter for each selected scent;
   e) applying liquids of the selected scents each on separate blotters;
   f) holding the blotters together in a grouping;
   g) waving the blotters to produce a mixture of all the selected scents;
   h) removing scents from the grouping that are no longer desired from the grouping;
   i) adding desired scents to the grouping to be part of the custom fragrance;
   j) determining an amount of each selected variable potency scent liquid using a prestored scent table;
   k) calculating the total number of drops "N" to be used for the selected container;
   l) determining the number of drops of all the variable potency scent liquids to be added to the selected container;
   m) subtracting the number of drops of the variable potency scent liquids intended to be used from the total number of drops for the selected container "N" to result in the remaining drops ($N_{remain}$);
   n) calculating the number of normal potency scent liquids selected (n) and dividing the remaining drops ($N_{remain}$) by the number of normal potency scent liquids selected (n) to result in the number of drops for each of the "n" normal potency scent liquids to add to the container;
   o) mixing the determined amounts of each selected scent liquids with a filler material in the selected container to result in the container filled with a mixture of scented liquids that have the custom fragrance.

2. The method of claim 1 wherein the step of selecting a blotter for each scent comprises:
   selecting blotters having increased surface areas, as compared with a previous blotters being used, for scents the customer would like to increase; and
   selecting blotters having decreased surface areas, as compared with a previous blotters being used, for scents the customer would like to decrease.

3. The method of claim 1 wherein the step of applying liquids comprises:
   selecting a blotter having a size corresponding to how strong each selected scent is desired to be;
   dipping the blotter to a predetermined depth into a scent liquid corresponding to the selected scent.

4. The method of claim 3 wherein the selected blotters have markings indicating the depth in which the blotter is dipped into the scent liquid;
   the blotters corresponding to scents that the customer would like to increase are dipped to a deeper marking than those of scents that the customer would like to reduce; and
   the depth markings of each scent are used to select the amounts of the scent liquids used in creating the custom fragrance.

5. The method of claim 1 wherein the step of determining an amount of each selected scent liquid to use comprises the steps of:
   a) selecting a container to be used to hold the custom fragrance;
   b) identifying a volume of the selected container;
   c) looking up an amount of the scent liquid on the scent table for the selected container volume, to use for at least one variable potency scent;
   d) using the indicated amount as the determined amount for that variable potency scent; and
   e) repeating steps "c" and "d" for at least one additional selected scent.

6. The method of claim 1 wherein the filler material is a denatured alcohol solution.

7. The method of claim 1 wherein the filler material is a topical oil base.

8. The method of claim 1 wherein the filler material is a wax-based substance.

9. The method of claim 1 wherein the volatility categories are based upon molecular weight.

10. The method of claim 1 wherein the families comprise at least one of the following: the citrus family including lemon and orange scents; the herbal family, including lavender, mint and basil scents; the fresh/clean family; the fruity family, including berry and tropical scents; the floral family including flower scents, the gourmand family, including honey, vanilla and cinnamon; and the earth family, including woody scents.

11. The method of claim 1 wherein the scent table indicates an amount of each scent to use for a given scent strength.

12. The method of claim 1 wherein the entries in the scent table are an inverse measure of the strength of each scent.

* * * * *

UNITED STATES PATENT AND TRADEMARK OFFICE
CERTIFICATE OF CORRECTION

PATENT NO. : 10,242,391 B2
APPLICATION NO. : 14/936662
DATED : March 26, 2019
INVENTOR(S) : Fleming It is certified that error appears in the above-identified patent and that said Letters Patent is hereby corrected as shown below:

On the Title Page

Item (12) delete "Fleming, et al." and insert -- Fleming --.

Item (72) Inventors should read:
-- (72) Inventor: Danielle K. Fleming, Dunmore, (PA) --.

Signed and Sealed this
Twenty-first Day of April, 2020

Andrei Iancu
*Director of the United States Patent and Trademark Office*